United States Patent [19]

Kiy et al.

[11] Patent Number: 6,140,365
[45] Date of Patent: Oct. 31, 2000

[54] PREPARATION OF MICROORGANISMS COMPRISING OMEGA-3-FATTY ACID FOR USE AS A PROPHYLACTIC OR THERAPEUTIC AGENT AGAINST PARASITIC DISEASES OF ANIMALS

[75] Inventors: Thomas Kiy, Frankfurt; Ulrich Klein, Kelkheim; Stefan Müllner, Hochheim; Dieter Wullbrandt, Hofheim, all of Germany

[73] Assignee: Adventis Research & Technologies GmbH & Co. KG, Frankfurt am Main, Germany

[21] Appl. No.: 09/230,182

[22] PCT Filed: Jul. 21, 1997

[86] PCT No.: PCT/EP97/03905

§ 371 Date: Feb. 18, 1999

§ 102(e) Date: Feb. 18, 1999

[87] PCT Pub. No.: WO98/03168

PCT Pub. Date: Jan. 29, 1998

[30] Foreign Application Priority Data

Jul. 22, 1996 [DE] Germany ............... 19629433

[51] Int. Cl.[7] ............... A61K 31/20; C12P 7/64
[52] U.S. Cl. ............... 514/560; 435/134
[58] Field of Search ............... 514/560; 435/134

[56] References Cited

U.S. PATENT DOCUMENTS

| 4,374,657 | 2/1983 | Schendel et al. ............... 62/19 |
| 5,130,242 | 7/1992 | Barclay ............... 435/134 |

FOREIGN PATENT DOCUMENTS

| 1294216 | 1/1992 | Canada . |
| WO 91/07498 | 5/1991 | WIPO . |
| WO 93/00084 | 1/1993 | WIPO . |

OTHER PUBLICATIONS

Allen, P., et al., "Diets High in n–3 Fatty Acids Reduce Cecal Lesion Scores in Chickens Infected with *Eimeria tenella*," Poultry Science, vol. 75, No. 2, pp. 179–185 (1996).

Ukoha, A., "Trypanocidal Action of Polyunsaturated Fatty Acids and Lysophosphatidyl–choline Derivatives," Database Cab Abstracts, Dialog An=2643290, XP002047888 (1990).

"Preparation of New Highly Unsaturated Fatty Acid . . . Comprising Arachindonic Acid Producing Microbe Which Acts as Culture Medium," Database WPI; AN 92–027351, XP002047889 (1991).

Patent Abstracts of Japan, Publication No. JP 01 215245 (Aug. 29, 1989).

"Manufacture of Highly Unsaturated Fatty Acid—By Aerobic Culture of Protozoa Euglena in Medium Culture Containing Linolic, Oleic or Alpha–linolenic Acid," Database WPI; AN 86–249481, XP002047890 (1986).

Kiffe, M., et al., "Purification of Docosahexaenoic Acid (DHA) Produced by Marine Microalga *Isochrysis galbana*," J. Marine Biotechnol., vol. 2, No. 3, pp. 139–142 (1995).

Lopez, D. A., et al., "Improvement of Eicosapentaenoic Acid Content in Isolates of *Isochrysis galbana*," J. Marine Biotechnol., vol. 1, No. 3, pp. 147–149 (1993).

Takeyama, H., et al., "DHA Enrichment of Rotifers: A Simple Two–Step Culture Using the Unicellular Algae *Chlorella regularis* and *Isochrysis galbana*," J. Marine Biotechnol., vol. 3, No. 4, pp. 244–247 (1996).

Allen, P., et al., "Interaction of Dietary Flaxseed with Coccidia Infections in Chickens," Poultry Science, vol. 76, No. 6, pp. 822–827 (1997).

Patent Abstracts of Japan, Publication No. JP 08 133980 (May 28, 1996).

Kendrick, A., et al., "Lipids of Selected Molds Grown for Production of n–3 and n–6 Polyunsaturated Fatty Acids," Lipids, vol. 27, No. 1, pp. 15–20 (1992).

Patent Abstracts of Japan, Publication No. JP 04 088954 (Mar. 23, 1992).

*Primary Examiner*—Kevin E. Weddington
*Attorney, Agent, or Firm*—Foley & Lardner

[57] ABSTRACT

Preparation of microorganisms comprising omega-3-fatty acids for use as a prophylactic or therapeutic agent against parasitic diseases of animals The present invention relates to the use of a preparation of microorganisms containing omega-3-fatty acid for preparing a medicament for prophylactic and therapeutic use against a parasitic disease of animals.

31 Claims, 1 Drawing Sheet

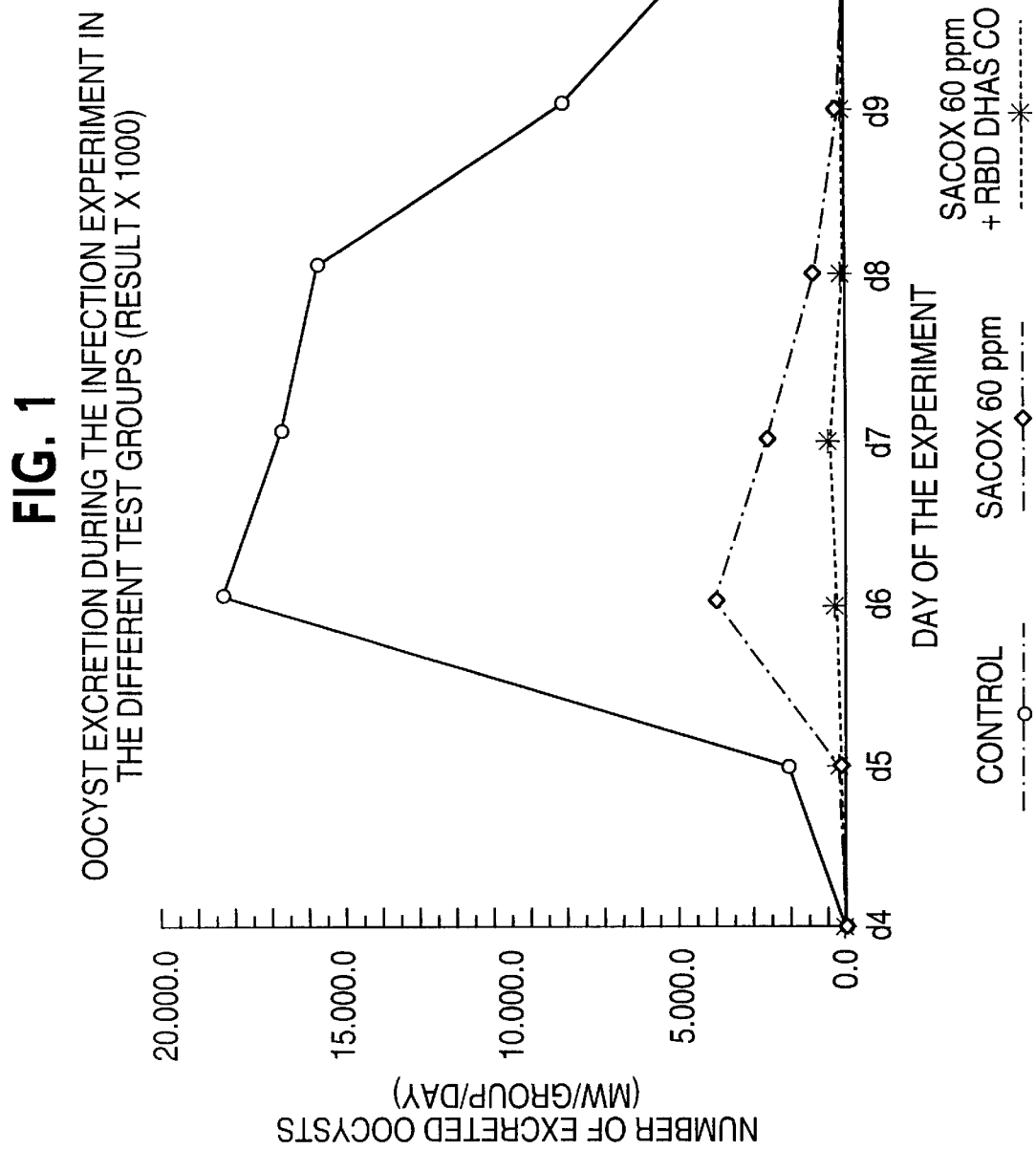

PREPARATION OF MICROORGANISMS COMPRISING OMEGA-3-FATTY ACID FOR USE AS A PROPHYLACTIC OR THERAPEUTIC AGENT AGAINST PARASITIC DISEASES OF ANIMALS

DESCRIPTION

Preparation of microorganisms comprising omega-3-fatty acids for use as a prophylactic or therapeutic agent against parasitic diseases of animals The present invention relates to the use of a preparation containing omega-3-fatty acid for preparing a medicament for prophylactic and therapeutic use against a parasitic disease of animals.

Omega-3-fatty acids (omega-3-polyunsaturated fatty acids=omega-3-PUFAs), in particular EPA (eicosapentaenoic acid) and DHA (docosahexaenoic acid), have recently become more and more important for the human diet. They have positive dietary and health-enhancing effects. With respect to lowering the cholesterol level and reducing the frequency of cardiovascular disorders, it is sensible to enrich the human diet with omega-3-fatty acids. The positive effect of omega-3-PUFAs on pathological metabolic processes has been demonstrated in a large number of studies. Moreover, docosahexaenoic acid plays an important role as a building block in the central nervous system (brain) and in the retina.

Hitherto, except for fish breeding, there have been relatively few investigations into the significance of omega-3-PUFAs in the field of animal health. Up to now, omega-3-PUFA preparations have been primarily administered to animals via the feed with the intention of enriching certain animal products (eggs, meat) intended for human consumption with omega-3-PUFAs. Thus, the omega-3-PUFA content of the fatty tissues of the muscles of poulards could be increased significantly by feeding them a PUFA-containing product (Mooney & van Elswyk, 1995, Poultry Science 74, Suppl. 1, 89). Furthermore, it was shown that it is possible to enrich eggs with omega-3-PUFAs by enriching the feed of laying hens with omega-3-PUFA-containing components (linseed oil, rapeseed oil, soya oil, fish oil) (Herber & van Elswyk, 1995, Poultry Science 74, Suppl. 1, S. 57;

Grashorn and Blanch 1996, DGS 6, 6–9).

Hitherto, there have been no investigations into the use of omega-3-PUFA preparations in the context of prophylactic and therapeutic measures for controlling parasitic diseases of useful animals. In modern poultry farming, coccidiosis caused by a certain protozoan species (order Eimeria) has great practical economical importance as an intestinal disease, owing to the high proportion of losses. In a study which has recently been published, it was shown that the course of a coccidia infection can be influenced positively by enriching the feed with fish oil (reduction in the number/intensity of the lesions in the intestine, reduction in weight loss) (Muirhead, 1995, Feedstuffs, Nov. 6 1995, 12). This effect was ascribed to the action of the omega-3-PUFAs present in fish oil.

Worm infections are widespread throughout the world among agriculturally useful animals and lead to economic losses, in particular among young animals.

Omega-3-PUFA preparations develop, in the digestive tract, an activity directed against helminths (worms) which parasitize there.

However, the use of fish oil as a source of omega-3-fatty acids is not unproblematic since, in addition to a number of other fatty acids, cholesterol and certain heavy metals are also present in fish oil. Moreover, the composition of the PUFA content varies, in some cases considerably, depending on the kind of fish, the season and the fishing area, which makes the preparation of PUFA products with a uniform concentration content from fish difficult. Furthermore, fish oil can be employed in the feed diets only in a limited amount, owing to the effect on the end products in terms of taste and smell. A further problem which has to be emphasized is the fact that the omega-3-PUFA concentration in fish oil is usually at most 15–20%, and it is technically very difficult to concentrate the fatty acids, which is necessary for preparing a feed additive.

The present invention solves the abovementioned problems by using aquatic microorganisms (microalgae, protozoa, fungi, bacteria) as production strains for preparing preparations comprising omega-3-PUFAs, in particular eicosapentaenoic acid (EPA) and docosahexaenoic acid (DHA). These preparations are employed as feed additives to develop their antiparasitic (in particular coccidiostatic) effect. The production strains are cultivated heterotrophically or autotrophically, harvested and subsequently dried and/or extracted. The PUFA preparations can be employed here in the form of biomass or oil as feed additive.

Consequently, the present invention specifically relates to the use of a preparation containing omega-3-fatty acid which is obtainable from aquatic microorganisms for preparing a medicament for prophylactic or therapeutic use against a parasitic disease of animals.

The preparation preferably comprises the biomass which is obtainable by cultivation of aquatic microorganisms, is present in the form of an oil, or both.

According to a particularly preferred embodiment of the present invention, the preparation containing omega-3-fatty acid is obtainable from heterotrophically cultivable microalgae, and these microalgae particularly preferably belong to the order Crypthecodinium or the order Euglena.

In a further preferred embodiment, the abovementioned preparation is obtainable from lower fungi, preferably of the orders Thraustochytrium or Mortierella.

In a further preferred embodiment of the present invention, the aquatic microorganisms belong to the photosynthesizing microalgae, which are preferably selected from the orders Phaeodactylum, Isochrysis, Monodus, Porphyridium, Spirulina, Chlorella, Botryococcus, Cyclotella, Nitzschia, Dunaliella and Nannochloropsis.

A further preferred embodiment provides that the abovementioned preparation is obtainable from bacteria, preferably selected from the orders Alteromonas and Shewanella.

The attached FIGURE, which forms part of this application, contains the graphic evaluation of the excretion of oocysts by chicken in a control group without administration of PUFA and in a group to which PUFA was administered.

Alternatively, the preparation is obtainable from mixtures of two or more different ones of the abovementioned aquatic microorganisms.

The preparation containing omega-3-fatty acid is particularly suitable for preparing a medicament for prophylactic and therapeutic use against avian coccidiosis.

The abovementioned preparation is furthermore also suitable for preparing a medicament for prophylaxis or therapy of an endoparasitic disease of large or small animals.

Consequently, the present invention also relates to a medicament for prophylactic or therapeutic use against a parasitic disease of animals which comprises an omega-3-fatty-acid-containing preparation which is obtainable as described above.

The medicament can also be combined with one or more other medicaments.

The medicament according to the invention for the therapy and prophylaxis of coccidiosis is particularly effective if it contains at least one further coccidiostat, preferably salinomycin.

The present invention will now be described in detail below.

Particularly suitable producers for preparing the omega-3-fatty-acid-containing preparation are heterotrophically growing microalgae and protozoa, such as Crypthecodinium and Euglena; lower fungi, such as Thraustochytrium, Schizochytrium and Mortierella; photosynthesizing microalgae of the orders Phaeodactylum, lsochrysis, Monodus, Porphyridium, Spirulina, Chlorella, Botryococcus, Cyclotella, Nitzschia, Dunaleilla and Nannochloropsis and bacteria, for example of the orders Alteromonas and Shewanella.

The preparation process of the omega-3-fatty-acid-containing preparation comprises the following steps:
- inoculation of the culture medium with the producer strain
- incubation of the culture under suitable conditions, it being possible for the cultivation to be carried out as a batch, feed-batch or continuous fermentation.
- harvest of the culture using, inter alia, the following methods: cryopelletization, filtration, centrifugation, spray-drying.
- if the biomass is not directly used as omega-3-PUFA preparation, an extraction step (for example supercritical $CO_2$ extraction or extraction with organic solvents) to obtain an extract may follow, using either the moist or the dried biomass.

The preparation in the form of an extract may optionally be purified prior to use, for example by SFC (supercritical fluid chromatography) or HPLC methods.

In the preparation according to the invention, the omega-3-PUFAs may be present, inter alia, in the form of phospholipids, glycolipids, mono-, di- or triglycerides or sulfolipids, or else as free acids or ethyl esters thereof.

The DHA or EPA content of the omega-3-PUFA preparation (biomass or oil) which is admixed to the feed is between 5 and 80%, based on the total fatty acid content.

The oil may furthermore be microencapsulated before use, to ensure better processing and a protection of the PUFAs. To increase the oxidative stability of the omega-3-PUFAs, it is possible to add stabilizers such as, for example, tocopherol and ascorbyl palmitate to the preparation.

The coccidiostatic action of the omega-3-fatty-acid-containing preparation is controlled using infection experiments with the target species poulards. The infective species used are *Eimeria acervulina, E. maxima* and *E. tenella*. The experiments are conducted for a period of 3 weeks. In the experiments, the effect of the PUFAs on the course of the infection is monitored at two different concentrations.

Administration and treatment plan:

| Treatment groups | Preparation | Number of animals | Dosage | Infection |
|---|---|---|---|---|
| A | Control | — | 15 | — | — |
| B | Treatment | yes | 15 | dose 1 | — |
| C | Treatment | yes | 15 | dose 2 | — |
| D | Control | — | 15 | — | Yes |
| E | Treatment | yes | 15 | dose 1 | Yes |
| F | Treatment | yes | 15 | dose 2 | Yes |

Various parameters are monitored during the studies. The following parameters indicate the effectiveness of the PUFAs:
- individual development of the weight of the animals
- oocyst excretion
- reduction of the lesions in the intestine (registered using the lesion score index)
- mortality rate Furthermore, it is possible to control the action of the coccidiostat salinomycin in combination with the omega-3-fatty-acid-containing preparation according to the present invention using sensitivity tests.

The damage to adult worms (therapeutic effect) and to developing worm stages (prophylactic effect) in a medium containing the preparation according to the invention can be tested in suitable in vitro test models using worms which do not live parasitically (for example *Caenorhabditis elegans*), or using exogenus stages of parasitic worms which develop in the environment (for example trichostrongylidae of the ruminants). The criteria used for the effectiveness of the preparation according to the invention are survival and mobility of the worms, and the rate of development of the juvenile stages.

Test

The effect of the combination PUFA (docosahexaenoic acid from Crypthecodinium) and salinomycin on the course of the infection after infection with *E. tenella* (Houghton, laboratory strain) was studied, with particular consideration of the individual total oocyst excretion in a feeding experiment with poulards.

Feeding a corn-rich diet (percentage of corn 44.6%), the effect of the combination docosahexaenoic acid/salinomycin on the Eimeria infection was studied in the experiment. To be able to draw a conclusion on the effect of the combination on the pathogenicity of the causative organism, the total oocyst excretion and the extent of the lesion scores in the caeca of each test animal were determined. The weight development and the feed conversion of the animals gave further indications on the extent of the infection.

| Characteristics of the study |
|---|
| Test period: 20 days |

Test preparations

| Name: | Sacox ® | RBD-DHASCO ® |
|---|---|---|
| | | docosahexaenoic acid |
| Concentration: | Active compound | contains 40% docosa- |
| | salinomycin | hexanoic acid (DHA) |
| Manufacturer: | HRVET | Martek Biosciences |
| | | Corporation, USA |

Test system

| Species: | Lohmann fattening chicken |
|---|---|
| Sex: | Male |
| Age: | One-day old chicken |

| Test phases | |
|---|---|
| Test phase | Day of test |
| Arrival of the animals/test start | d − 8 |
| Division into groups | |
| Group feces control for foreign infections | d − 3 |
| Labeling of the animals (poultry tags) | |
| Start of separate housing | |
| Infection of the animals (challenge) | d0 |
| Group feces control for foreign infections | d + 3 |
| Group feces collection (control groups) | d + 4 to d + 10 |
| Individual feces collection (infection groups) | |
| Determination of the total oocyst output | |
| Determination of the lesion score | d + 11 |

| Administration and treatment scheme | |
|---|---|
| Administration of Sacox ® + RBD-DHASCO ®: | orally with the feed |
| Infection with *E. tenella*, Houghton (laboratory strain): | orally by means of an oesophageal tube |
| Infection dose: | 500 sporolated oocysts/animal (in 1 ml of 1% w/v aqueous ox bile solution) |
| Age of the oocysts at infection: | 21 days |

| Groups | Name/feed ration | Preparation | n | Dosage | Infection |
|---|---|---|---|---|---|
| A | control/corn diet | — | 15 | — | — |
| B | Sacox | salinomycin | 15 | 60 ppm | — |
| C | Sacox/RBD-DHASCO | salin/DHA | 15 | 60 ppm/4% | — |
| D | control/corn diet | — | 15 | — | yes |
| E | Sacox | salinomycin | 15 | 60 ppm | yes |
| F | Sacox/RBD-DHASCO | salin/DHA | 15 | 60 ppm/4% | yes |

Work-up of the sample material

Feces collection

The feces were collected daily over a period of 24 hours in plastic bowls containing 4% strength potassium dichromate solution. All the feces were transferred to a collection vessel.

Work-up of the feces samples

The individual feces samples were stirred (magnetic stirrer, 250 rpm), sieved (mesh size 1 mm) and made up with conc. NaCl solution to a final volume of 300 or 800 ml (depending on the expected oocyst excretion). Subsequently, an excess of crystalline NaCl was added with stirring. During stirring, approximately 1 ml of the suspension (from the middle of the liquid column) was sampled using a pipette or a syringe, and the McMaster chamber was filled with this sample.

Counting of the oocysts

From the side facing the investigator, the chambers were filled bubble-free. Prior to filling, the cover glass was shifted such that an approximately 3 mm wide gap was formed above the chambers. Before counting, the cover glass was moved into its proper position (the chambers have to be covered completely). After flotation for about 5 minutes, the oocysts were counted in the 10 sections of the 3 counting nets, at a magnification of 80 or 320.

Taking into account the volume under each counting net (10 mm×10 mm×1.5 mm=0.15 ml) and the volume of the suspension, the number of oocysts was calculated.

Practice of the experiment

The entire experiment was carried out according to the principle of good laboratory practice.

The results are shown in the table below and in the FIGURE.

Weight development, feed intake, feed conversion and oocyst excretion

| | Life weight | | | Feed | | Oocyst |
|---|---|---|---|---|---|---|
| | Start g | End g | Increase g/d | intake g/d | conversion kgFl/kgLWI* | excretion x 1000/animals |
| A | 102 | 580 | 34 | 57 | 1.6 | |
| control | 100.0 | 100.0 | 100.0 | 100.0 | 100.0 | |
| B | 103 | 566 | 33 | 57 | 1.6 | |
| Sacox 60 ppm | 101.0 | 97.6 | 97.0 | 100.0 | 100.0 | |
| C | 100 | 571 | 34 | 56 | 1.5 | |
| Sacox 60 ppm + RBD-DHASCO 4% | 98.0 | 98.4 | 100.0 | 98.2 | 93.8 | |
| D | 102 | 560 | 33 | 56 | 1.6 | 62,795 |
| control Infection group | 100.0 | 96.6 | 97.0 | 98.2 | 100.0 | 100.0 |
| E | 103 | 551 | 32 | 56 | 1.6 | 6170 |
| Sacox 60 ppm Infection group | 101.0 | 95.0 | 94.1 | 98.2 | 100.0 | 9.8 |
| F | 100 | 577 | 34 | 55 | 1.5 | 605 |
| Sacox 60 ppm + RBD-DHASCO 4% Infection group | 98.0 | 99.5 | 100.0 | 96.5 | 93.8 | 1.0 |

*kg Fl/kg LWI = kg of feed intake/kg of live weight increase

What is claimed is:

1. A method of preventing or treating parasitic disease in animals comprising administering to an animal in need thereof, a pharmaceutically acceptable composition comprising omega-3-fatty acid, obtainable from aquatic microorganisms.

2. The method of claim 1, wherein the composition comprises biomass obtainable by cultivation of aquatic microorganisms.

3. The method of claim 1, wherein the composition is an oil.

4. The method of claim 1 wherein the composition comprises 40% DHA.

5. The method of claim 4, wherein the aquatic microorganisms are heterotrophically cultivable microalgae.

6. The method of claim 5, wherein the microalgae belong to the order Crypthecodinium.

7. The method of claim 5, wherein the microalgae belong to the order Euglena.

8. The method of claim 1, wherein the aquatic microorganisms are lower fungi.

9. The method of claim 8, wherein the lower fungi belong to the order Thraustochytrium.

10. The method of claim 8, wherein the lower fungi belong to the order Mortierella.

11. The method of claim 1, wherein the aquatic microorganisms are photosynthesizing microalgae.

12. The method of claim 11, wherein wherein the microalgae are selected from the group of orders consisting of Phaeodactylum, Isochrysis, Monodus, Porphyridium, Spirulina, Chlorella, Botryococcus, Cyclotella, Nitzschia, Dunaliella and Nannochloropis.

13. The method of claim 1, wherein the aquatic microorganisms are bacteria.

14. The method of claim 13, wherein the bacteria are selected from the group of orders consisting of Alteromonas and Shewanella.

15. The method of claim 1, wherein the composition is obtainable from mixtures of two or more different aquatic microorganisms.

16. The method of claim 1, wherein the parasitic disease is avian coccidiosis.

17. The method of claim 1, wherein the parasitic disease is an endoparasitic disease of large or small animals.

18. A pharmaceutical composition for prophylactic or therapeutic use against a parasitic disease in animals which comprises a disease preventing or treating effective amount of an omega-3-fatty-acid-containing preparation obtainable from aquatic microorganisms and at least one further coccidiostat.

19. The composition of claim 18 further comprising at least one other ingredient.

20. The composition of claim 19, wherein said composition comprises salinomycin.

21. The composition of claim 18, which comprises a biomass obtainable from aquatic microorganisms.

22. The composition of claim 18, which is an oil.

23. The composition of claim 18, wherein said aquatic microorganisms are heterotrophically cultivable microalgae.

24. The composition of claim 23, wherein said microalgae is from an order selected from the group consisting of Crypthecodiniam and Euglena.

25. The composition of claim 18, wherein the aquatic microorganism is a lower fungus.

26. The composition of claim 25, wherein said lower fungus belongs to the order Thraustochytrium or Mortierella.

27. The composition of claim 18, wherein said microorganisms are photosynthesizing microalgae.

28. The composition of claim 27, wherein the microalgae are from an order selected from the group of orders consisting of Phaeodactylum, Isochrysis, Monodus, Porphyridium, Spirulina, Chlorella, Botryococcus, Cyclotella, Nitzschia, Dunaliella and Nannochloropsis.

29. The composition of claim 18, wherein said microorganisms are bacteria.

30. The composition of claim 29, wherein said bacteria are from the order Alteromonas or Shewanella.

31. The composition of claim 18, wherein the preparation is obtainable from one or more aquatic microorganisms.

* * * * *